United States Patent
Chen

[19]

[11] Patent Number: 5,913,103
[45] Date of Patent: Jun. 15, 1999

[54] METHOD OF DETECTING METAL CONTAMINANTS IN A WET CHEMICAL USING ENHANCED SEMICONDUCTOR GROWTH PHENOMENA

[75] Inventor: Chun Ya Chen, San Jose, Calif.

[73] Assignee: Integrated Device Technology, Inc., Santa Clara, Calif.

[21] Appl. No.: 08/855,515

[22] Filed: May 13, 1997

[51] Int. Cl.$^6$ .................................................. H01L 21/00
[52] U.S. Cl. ............................................................... 438/14
[58] Field of Search ........................................ 438/14, 16

[56] References Cited

U.S. PATENT DOCUMENTS

| | | |
|---|---|---|
| 4,878,988 | 11/1989 | Hall . |
| 5,066,359 | 11/1991 | Chiou . |
| 5,130,260 | 7/1992 | Suga . |
| 5,147,826 | 9/1992 | Liu . |
| 5,164,093 | 11/1992 | Chilton . |
| 5,194,397 | 3/1993 | Cook . |
| 5,207,863 | 5/1993 | Kumomi . |
| 5,244,819 | 9/1993 | Yue . |
| 5,272,119 | 12/1993 | Falster . |
| 5,274,434 | 12/1993 | Morioka . |
| 5,352,636 | 10/1994 | Beinglass . |
| 5,356,830 | 10/1994 | Yoshikawa . |
| 5,418,172 | 5/1995 | Falster . |
| 5,501,767 | 3/1996 | Sorensen . |
| 5,516,730 | 5/1996 | Saeed . |
| 5,628,954 | 5/1997 | Sato ............................................ 438/16 |

FOREIGN PATENT DOCUMENTS 5-198579  8/1993  Japan .

*Primary Examiner*—Brian Dutton
*Attorney, Agent, or Firm*—Pillsbury, Madison & Sutro

[57] ABSTRACT

The present invention uses a clean semiconductor substrate, typically in wafer form, and applies to the surface of the semiconductor a wet chemical that is suspected of containing a contaminant. After drying of the wet chemical, a high temperature, low pressure chemical vapor deposition of a semiconductor material is performed. Metal contaminants that exist on the surface of the semiconductor substrate act as seeds to initiate crystal growth of the semiconductor material that is being deposited. Due to the enhanced crystal growth of the semiconductor material at locations corresponding to positions of the metal contaminant on the semiconductor substrate, a visual inspection of the resulting surface of the semiconductor will indicate the presence of a metal contaminant.

22 Claims, 11 Drawing Sheets

100 X

300 X

CHEMICAL:   100:1 HYDROFLUORIC ACID

| SAMPLE ID: | | DL' | N BAY SINK TS1 |
|---|---|---|---|
| ALUMINUM | (Al) | 0.1 | 0.6 |
| BORON | (B) | 2.0 | <2.0 |
| CALCIUM | (Ca) | 3.0 | <3.0 |
| CHROMIUM | (Cr) | 0.1 | <0.1 |
| COPPER | (Cu) | 0.1 | (6.3) |
| IRON | (Fe) | 2.0 | <2.0 |
| LEAD | (Pb) | 0.1 | <0.1 |
| LITHIUM | (Li) | 0.05 | <0.05 |
| MAGNESIUM | (Mg) | 0.1 | 0.3 |
| MANGANESE | (Mn) | 0.1 | <0.1 |
| NICKEL | (Ni) | 0.1 | <0.1 |
| POTASSIUM | (K) | 3.0 | <3.0 |
| SODIUM | (Na) | 0.1 | 0.9 |
| TIN | (Sn) | 0.05 | <0.05 |
| TITANIUM | (Ti) | 1.0 | <1.0 |
| ZINC | (Zn) | 1.0 | 1.6 |
| TUNGSTEN | (W) | 2.0 | <2.0 |

FIG. 8

METHOD OF DETECTING METAL CONTAMINANTS IN A WET CHEMICAL USING ENHANCED SEMICONDUCTOR GROWTH PHENOMENA

FIELD OF THE INVENTION

The present invention relates to a method of detecting metal contaminants in a wet chemical by using an enhanced semiconductor growth phenomena. More particularly, the present invention relates to a method of detecting metal contaminants in a wet chemical using a high temperature, low pressure chemical vapor deposition process.

BACKGROUND OF THE RELATED ART

In the manufacture of semiconductor devices, many various processing steps exist, such as etching, deposition of polysilicon and oxide materials, the application and removal of masks, and the application and removal of metal materials. Each of these different processes that occur during the fabrication of a semiconductor circuit require the use of very specialized materials that must meet very stringent standards of purity. Despite the very stringent standards of purity that are maintained during the fabrication of semiconductor circuits, there are times when contaminants are undesirably introduced, thus causing the manufacture of defective semiconductor circuits.

Once it has been determined that a lot of semiconductor circuits is defective, it is known to check whether a new batch of a recently introduced material contains contaminants that are causing the defect. With respect to wet chemical materials, this testing, as is conventionally performed, requires that a sample of the newly introduced batch of wet chemical material be delivered to an independent analysis laboratory which performs a series of analytical composition tests to identify the percentage of each different type of element in the wet chemical material.

While the above conventional test effectively indicates whether a batch of a newly introduced wet chemical material contains contaminants, this conventional test requires that a sample of the wet chemical be sent out to an independent laboratory for this analysis, and the analysis typically takes one to two days to complete. As a result, during the period of time that this test is being performed, the semiconductor processing equipment that is being used to produce the semiconductor circuits typically remains idle. This down time of at least a day or two before the problem can be discovered is undesirably long.

Accordingly, a quicker method of detecting contaminants in materials is desirable.

SUMMARY OF THE INVENTION

It is an object of the invention to provide a method of quickly determining the presence of a metal contaminant in a wet chemical material.

It is a further object of the present invention to provide a method of detecting metal contaminants in a wet chemical that can be performed in the production facility where the semiconductor circuits are being manufactured.

It is a further object of the present invention to provide a method that allows for the visual detection, without magnification, of enhanced crystal growth that indicates the presence of a metal contaminant.

In order to achieve the above objects of the invention, among others, the present invention uses a clean semiconductor substrate, typically in wafer form, and applies to the surface of the semiconductor a wet chemical that is suspected of containing a contaminant. After drying of the wet chemical, a high temperature, low pressure chemical vapor deposition of a semiconductor material is performed, preferably using a polysilicon material. Due to the high temperature and low pressure that is used during the this deposition process, metal contaminants that exist on the surface of the semiconductor substrate act as seeds to initiate crystal growth of the semiconductor material that is being deposited. Due to the enhanced crystal growth of the semiconductor material at locations corresponding to positions of the metal contaminant on the semiconductor substrate, a visual inspection of the resulting surface of the semiconductor will indicate the presence of a metal contaminant. Thus, the existence of the enhanced crystal growth will indicate that a metal contaminant exists in the batch of the wet chemical.

Thus, if a metal contaminant is detected, the wet chemical material containing the contaminant can be removed, a substitute of the same material, without a contaminant, can be introduced, and production can continue. If, however, the test does not indicate the existence of enhanced crystal growth, it can be assumed that a metal contaminant does not exist and that something else is causing the production of defective semiconductor circuits.

Thus, the present invention can provide a manner of quickly determining the presence of metal contaminants in a wet chemical and allow for minimized down time of a production line.

BRIEF DESCRIPTION OF THE DRAWINGS

These and other objects, features and advantages of the present invention are better understood by reading the following detailed description of the preferred embodiment, taken in conjunction with the accompanying drawings, in which:

FIG. 8 illustrates a table identifying percentages of elements in a wet chemical containing the metal contamination illustrated in FIGS. 6A–6E.

DETAILED DESCRIPTION OF THE PREFERRED EMBODIMENT

Figure 1:
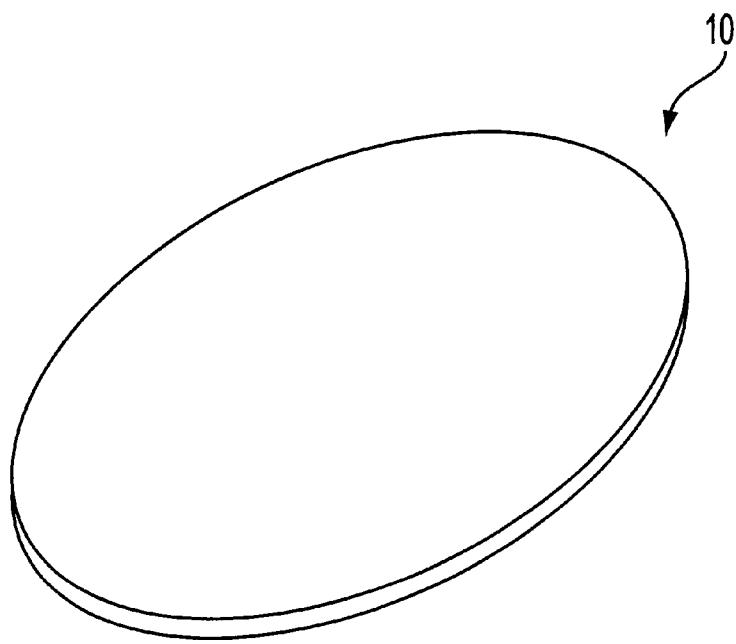
FIG. 1 is an illustration of an unprocessed semiconductor wafer substrate.

FIG. 1 illustrates an unprocessed semiconductor wafer 10. Of note, semiconductor wafer 10 has a smooth shiny surface appearance in the unprocessed state and contains no irregularities, protrusions, or other surface defects.

Figure 2:
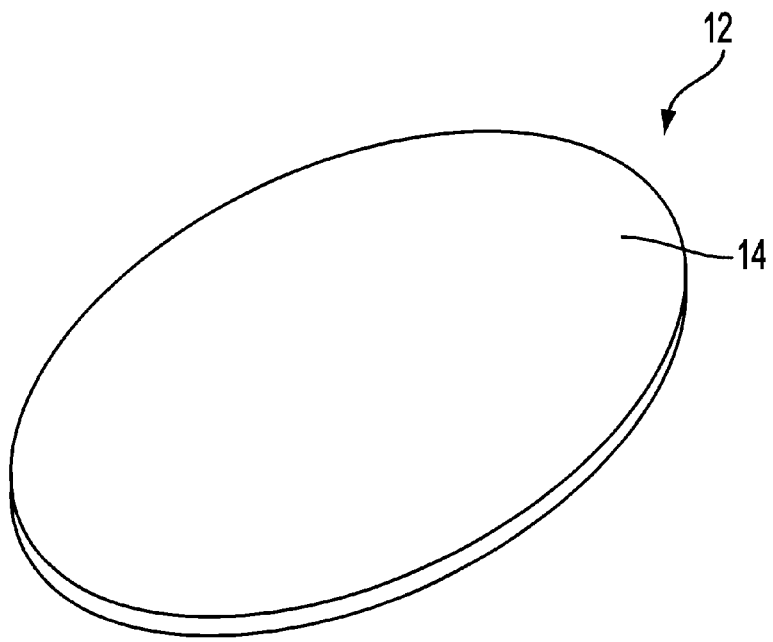
FIG. 2 illustrates a semiconductor wafer substrate to which a wet chemical containing no contaminant has been applied and then processed according to the present invention.

FIG. 2 illustrates a semiconductor wafer 12 that has been processed according to the present invention, as will be described further hereinafter, in which the semiconductor wafer 12 was subjected to a wet chemical that did not have any undesirable contaminants. Of note, semiconductor wafer 12 contains a surface 14 that is also smooth and has no surface defects.

Figure 3:
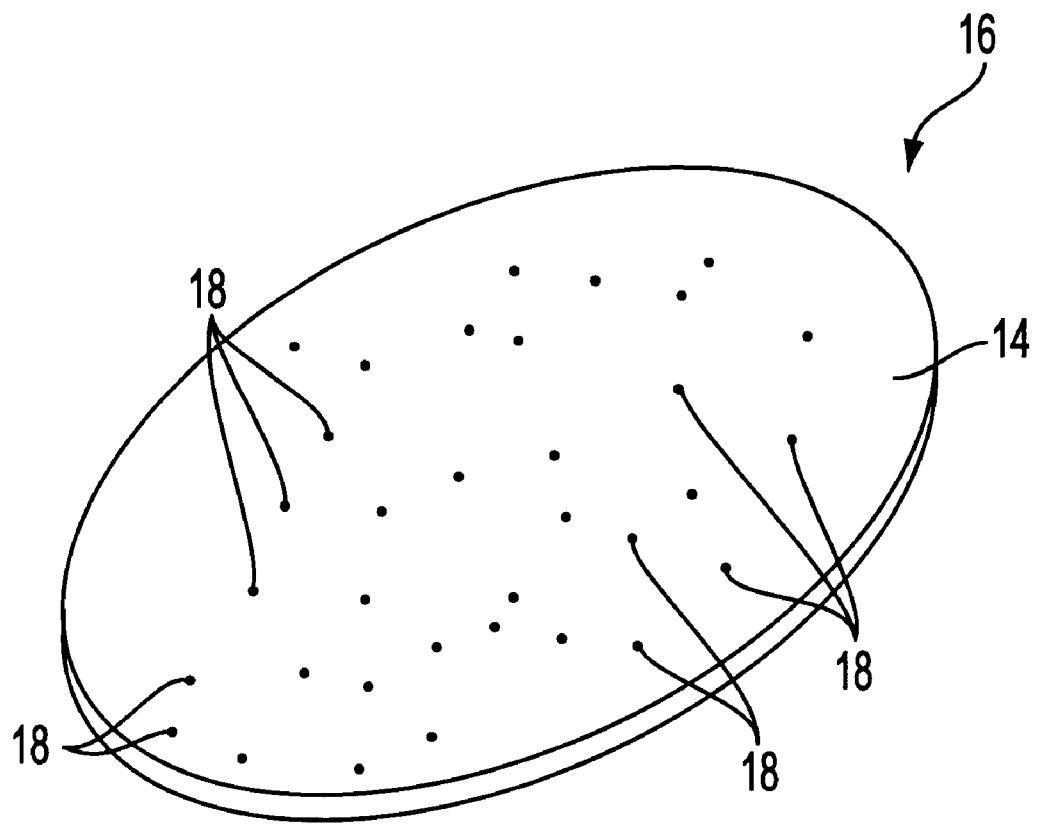
FIG. 3 illustrates a semiconductor wafer substrate to which a wet chemical containing a metal contaminant has been applied and then processed according to the present invention.

FIG. 3 illustrates a semiconductor wafer 16 that has been processed according to the present invention, as described further hereinafter, in which the wafer was subjected to a wet chemical that contained a undesired metal contaminant. Thus, while the semiconductor wafer 16 contains areas 14 that are smooth, which areas 14 correspond to the areas 14 illustrated in FIG. 2, there also exists irregular protrusions 18, at various locations on the semiconductor wafer 16. These irregular protrusions 18 typically will be noticeable at various locations over the entire surface of the semiconductor wafer 16, as illustrated.

Figure 4:
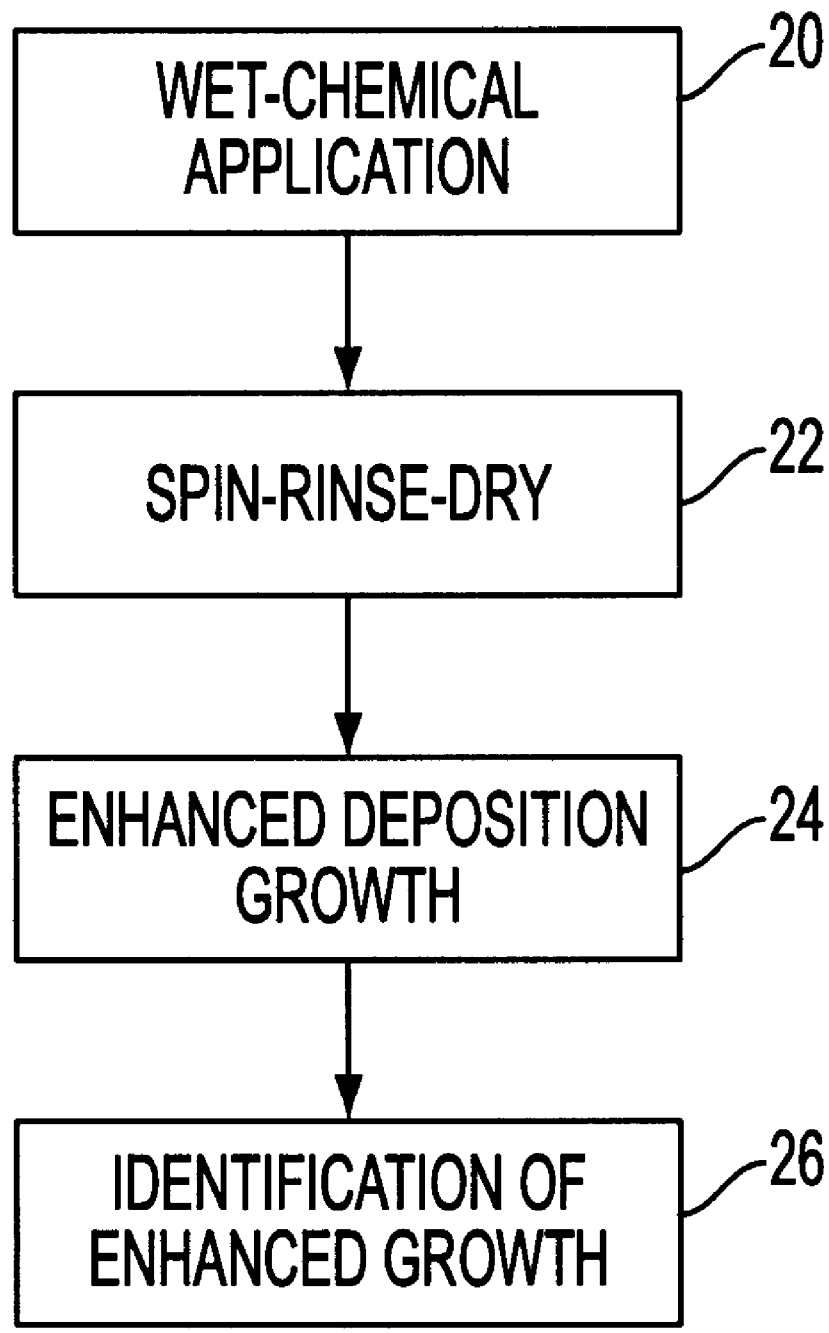
FIG. 4 is a flow chart illustrating the steps used for detecting a metal contaminant according to the preferred embodiment of the present invention.

FIG. 4 illustrates a flow chart of the method steps according to the preferred embodiment of the present invention, which allows for the detection of a metal contaminant in a wet chemical.

A wet chemical application step 20 initiates the process and subjects a semiconductor wafer, such as wafer 10 illustrated in FIG. 1, to a wet chemical. After being subjected to the wet chemical, a conventional spin-rinse-dry process 22 takes place so that the applied wet chemical can be dried. This spin-rinse-dry step will typically take about 5 to 10 minutes to complete.

Thereafter follows an enhanced deposition growth step 24 in which the wafer having the dried wet chemical is placed in a chemical vapor deposition chamber and then a semiconductor material is deposited onto the wafer at a high temperature and a low pressure, preferably using chemical vapor deposition. The chemical vapor deposition process preferably applies a polysilicon semiconductor material at a low pressure, preferably less than 1 TORR and a temperature that is preferably in the range of 600 to 675 degrees Celsius, for a time that is less than 10 minutes, and usually between 1–5 minutes.

Under the above described conditions, any metal contaminants that exist on the surface of the semiconductor wafer that has been placed into the chemical vapor deposition chamber will act as seeds and cause enhanced crystal growth of the polysilicon that is being deposited at locations corresponding to the positions of the metal contaminants on the surface of the semiconductor wafer.

While the conditions described above are the preferred ranges of temperature, pressure, time, and applied semiconductor material, variations of each of these different process parameters and materials is contemplated as being within the intended scope of the present invention. It is anticipated, however, that at temperatures less than 400 degree Celsius and for pressures that are greater than 5 TORR, that the enhanced growth of the polysilicon material will not take place. Accordingly, pressures of less than 5 TORR and temperatures greater than 400 degrees Celsius are preferred.

After the enhanced deposition growth step 24, an identification of undesired growth step 26 takes place. In this step, the wafer that has been subjected to the enhanced deposition growth step 24 is viewed to determine whether enhanced growth exists, due to the presence of undesired metal contaminants that act as seeds for enhanced crystal growth.

While a visual inspection without any magnification of the wafer that has been subjected to enhanced deposition growth will normally provide an indication of the existence of a metal contaminant due to the different appearance of the surface of the semiconductor wafer, viewing portions of the semiconductor wafer under magnification can assist in this regard.

So that an appreciation of the enhanced crystal growth that takes place according to the present invention can be obtained, a comparison will now be made of a semiconductor device 32 that has been partially processed and, at a point in the process, subjected to a metal contaminant. Thereafter semiconductor device 32 was subjected to an enhanced deposition growth step such as described as enhanced deposition growth step 24 in FIG. 4. The resulting protrusions 18, such as illustrated in FIG. 3, appear on semiconductor device 32 and can be seen at different levels of magnification. Furthermore, so that an appreciation of what these undesired enhanced growth protrusions 18 look like, a similar partially processed semiconductor device 30, without having had metal contaminants introduced, and at the same stage of processing, is shown to further illustrate the visual differences between a semiconductor wafer that contains a contaminant and a semiconductor wafer that does not contain a contaminant. While these pictures illustrate the presence of a contaminant in a semiconductor device that has been partially processed, it should be readily recognized that such a contaminant will be more readily apparent on a clean semiconductor wafer such as semiconductor wafer 10 illustrated in FIG. 1.

Figures 1, 5A:
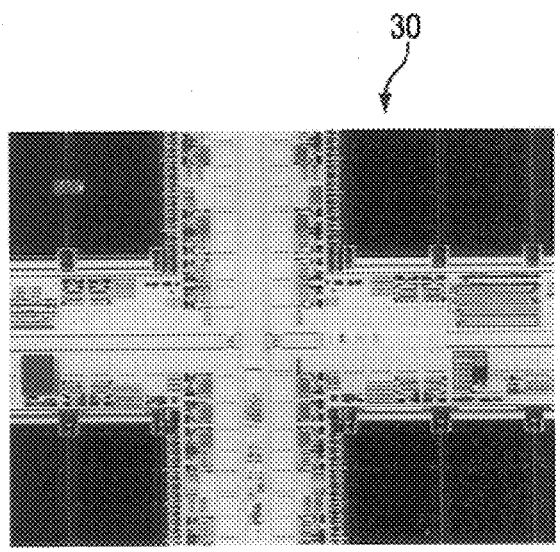
FIGS. 5A–5C illustrate different views of a partially processed semiconductor device, at various degrees of magnification, and having had no metal contaminants introduced during processing.
Figures 2, 5A:
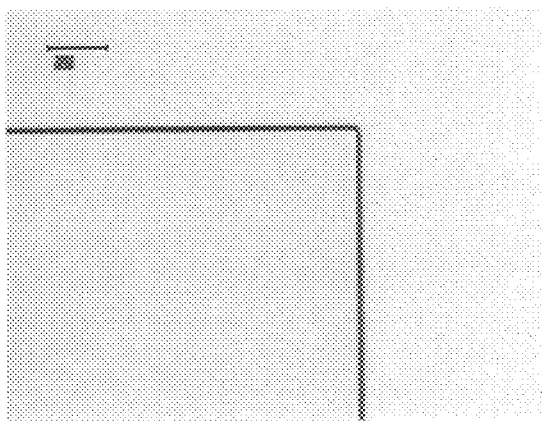
Figures 3, 5A:
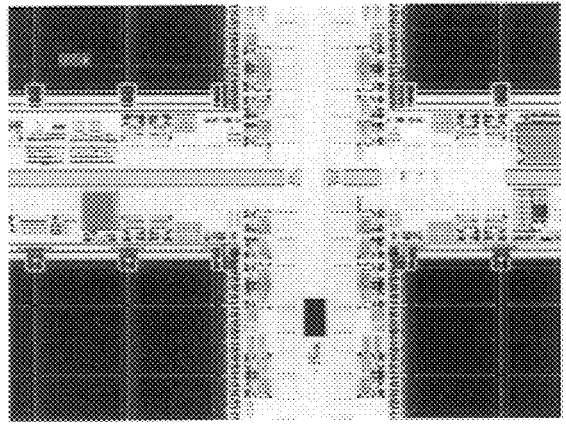
Figures 4, 5A:
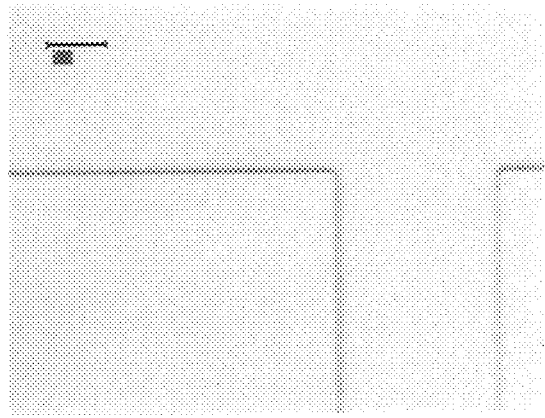
Figures 1, 2, 3, 4, 5B:
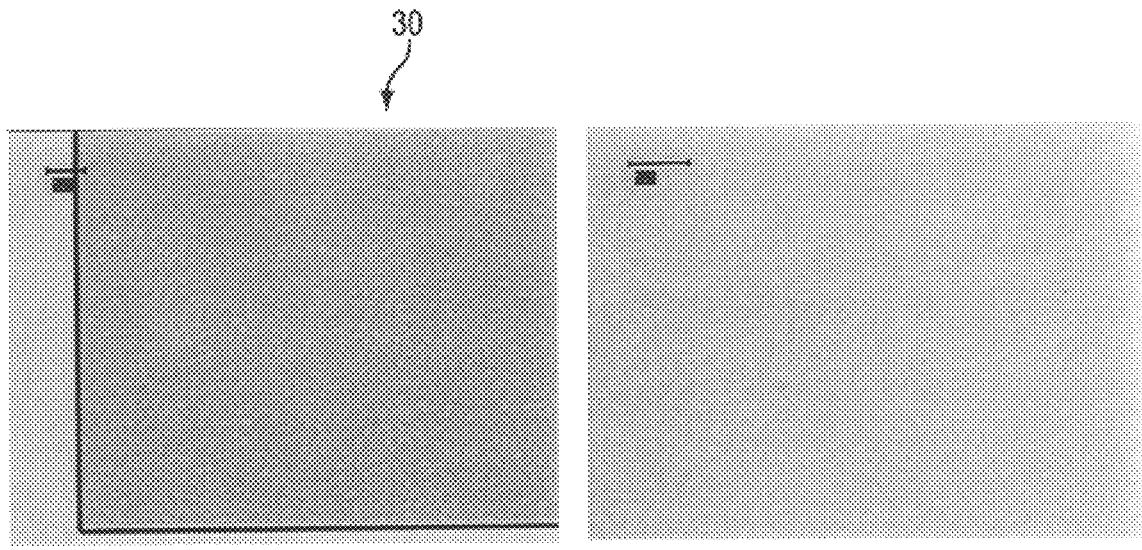
Figure 5C:
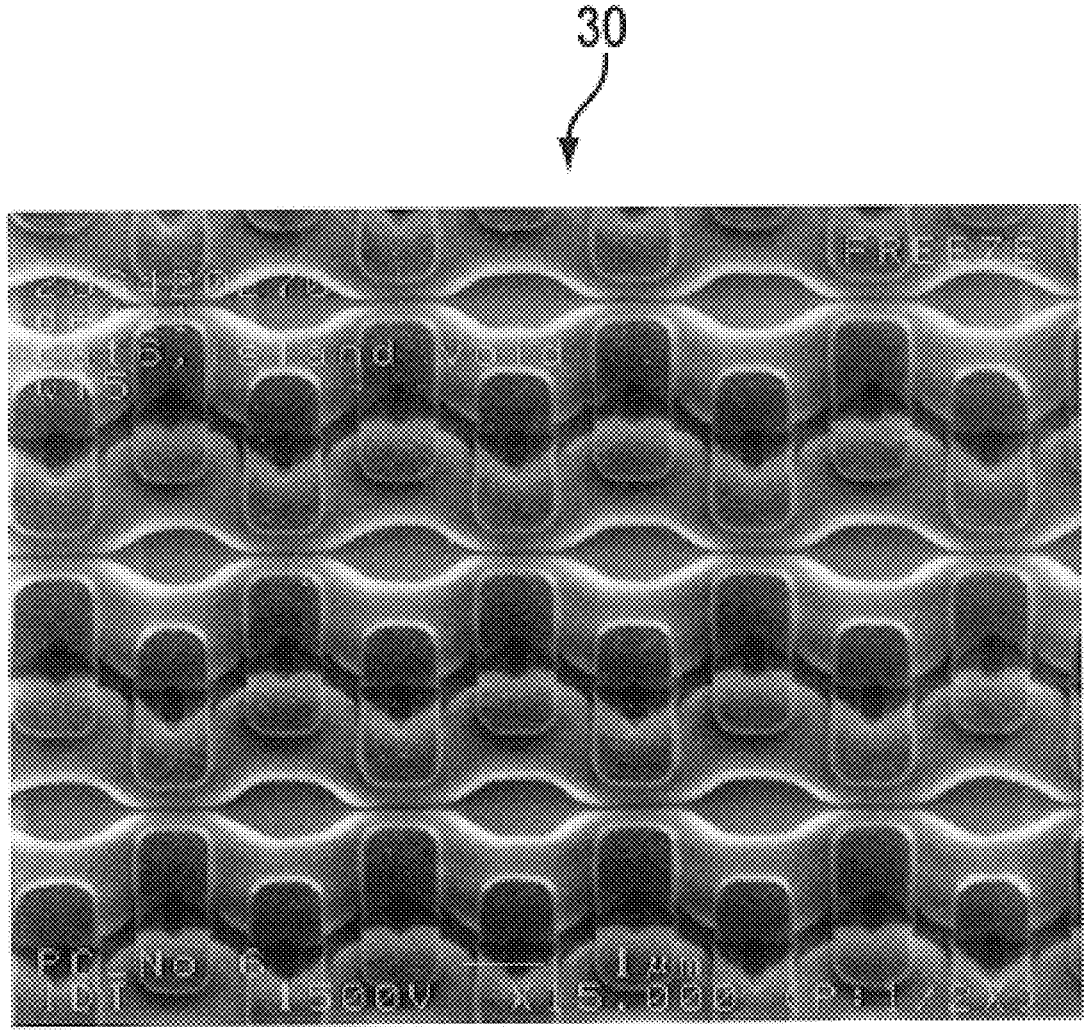

FIGS. 5A, 5B and 5C illustrate a partially processed semiconductor device 30 at, respectively, magnifications of 100×, 300×, and 15,000×. Of note, in each of these illustrations, clean, crisp images of the underlying structure of the semiconductor device as processed are readily apparent. In contrast, FIGS. 6A–6E illustrate, at various magnifications, the enhanced polysilicon crystal growth due to the presence of a metal contaminant on the surface of the semiconductor device 30, which has then been processed using an enhanced deposition growth step 24 such as previously described with respect to the enhanced growth deposition step 24 in FIG. 4.

Figures 1, 6A:
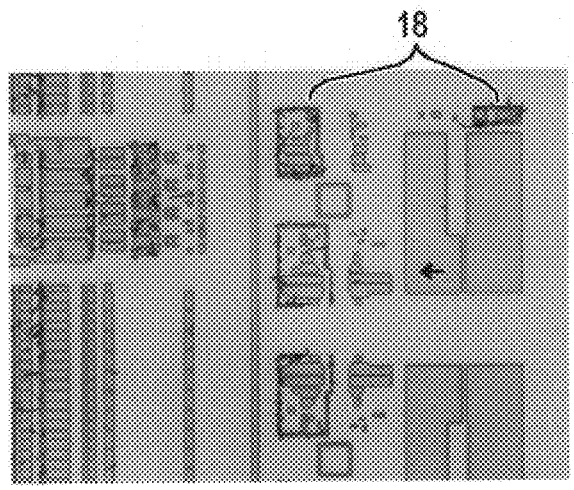
FIGS. 6A–6E illustrate different views of a partially processed semiconductor device, at various magnifications, and having had a metal contaminant introduced during processing and then being subjected to enhanced crystal growth according to the present invention.
Figures 2, 6A:
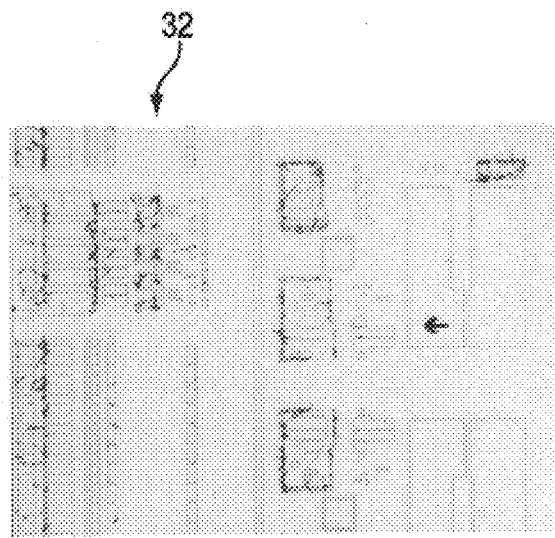
Figures 3, 6A:
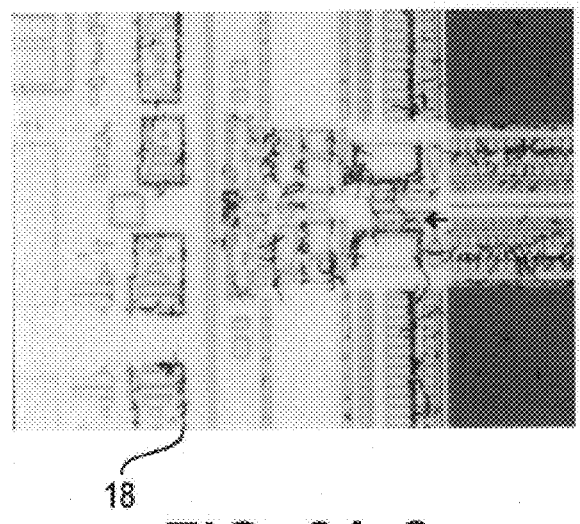
Figures 4, 6A:
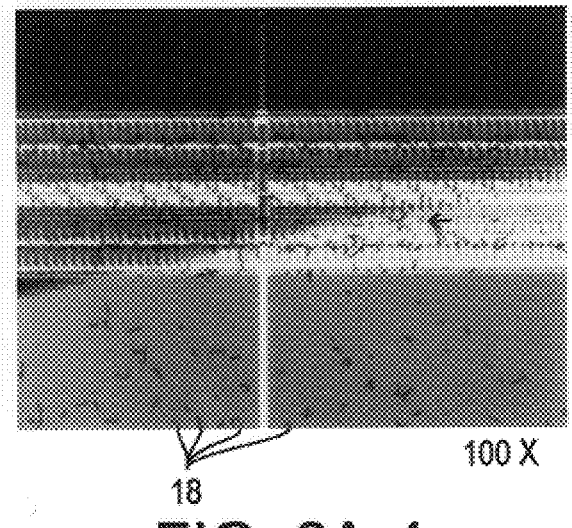
Figure 6B:
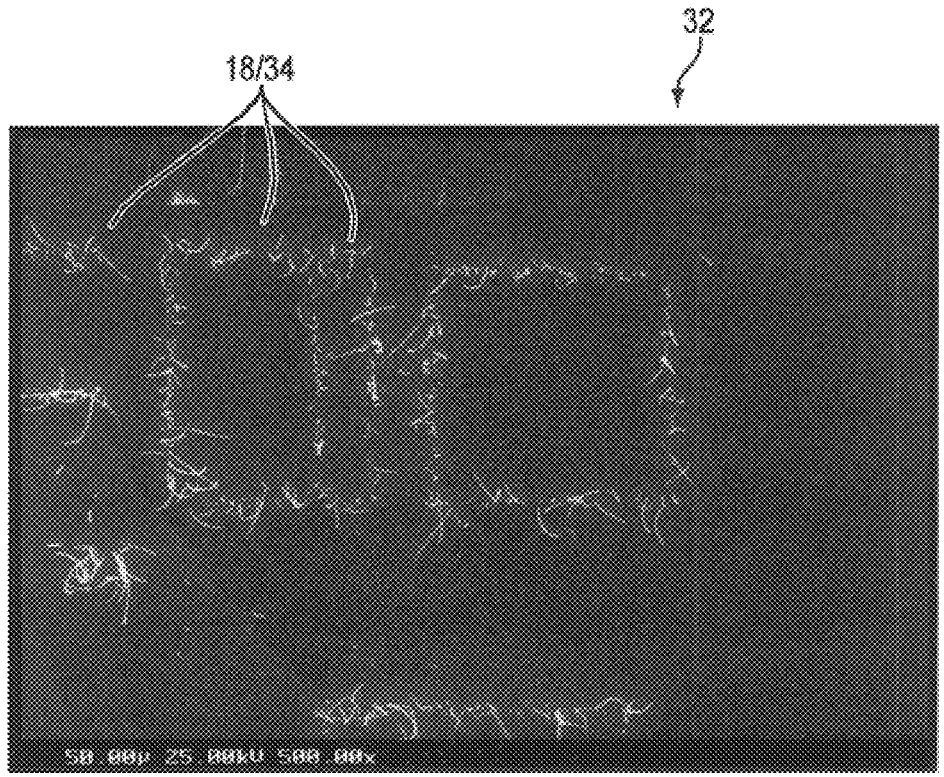
Figure 6C:
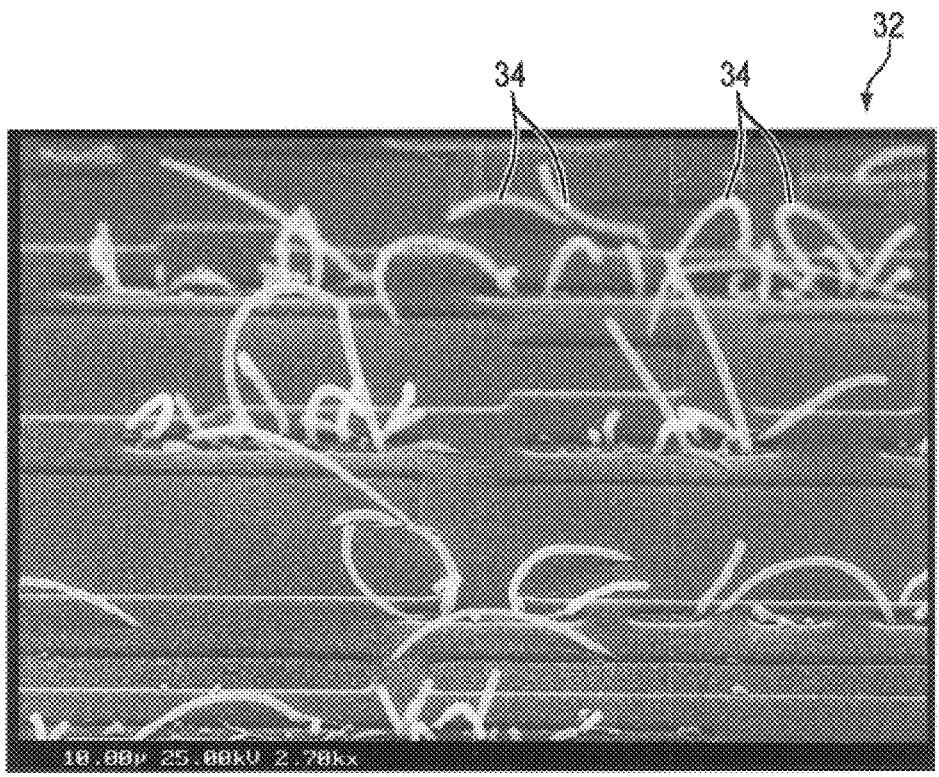
Figure 6D:
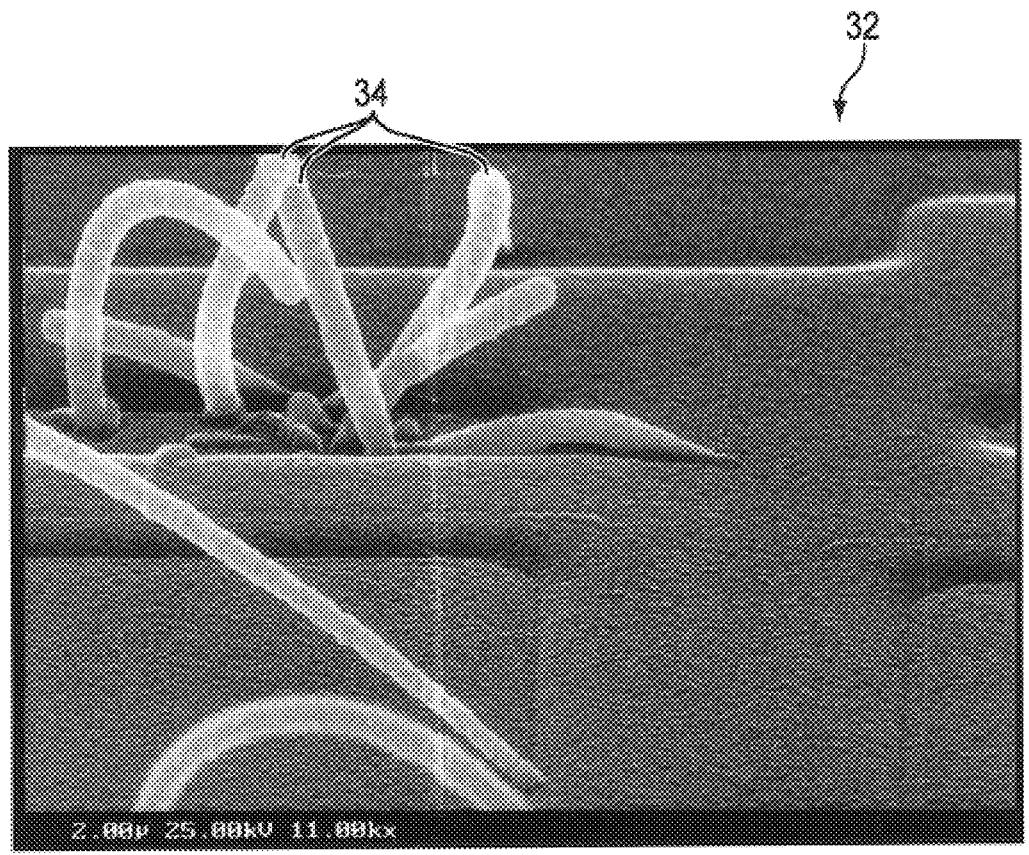
Figure 6E:
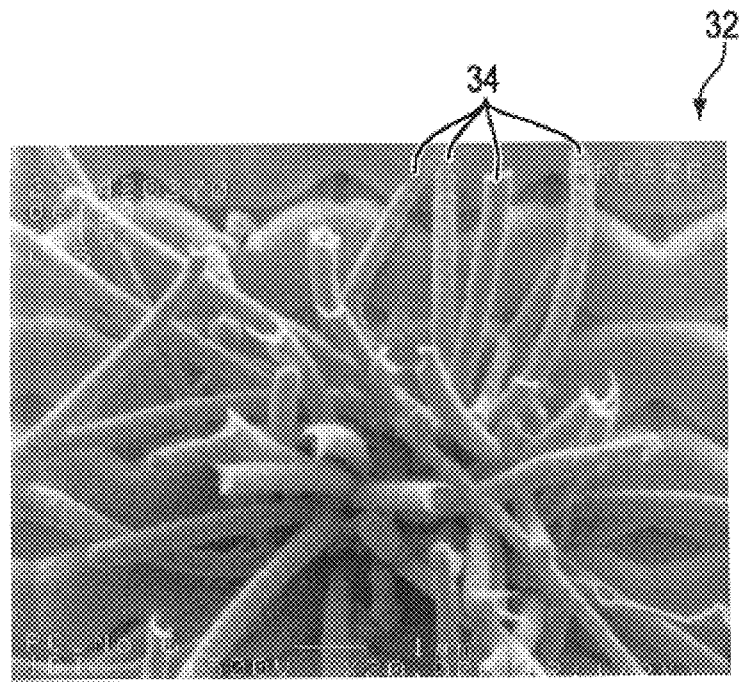

FIGS. 6A, 6B, 6C, 6D, and 6E, at, respectively, 100×, 500×, 2,700×, 11,000×, and 20,000× magnification, illustrate the presence of the undesired protrusions 18 of enhanced crystal growth that occur as a result of the metal contaminant on the surface of the semiconductor device acting as a seed, and thus causing the enhanced crystal growth of polysilicon material. At 100 × magnification, as illustrated in FIG. 6A, the undesired protrusions 18 appear as bumps on what would otherwise be an extremely smooth and crisp looking surface, as can be seen when contrasting FIGS. 6A and 5A. Furthermore, a contrast of FIG. 5C, which is at 15,000× magnification, with FIGS. 6D and 6E, which are at 11,000 and 20,000× magnification, clearly illustrates individual whiskers 34 of polysilicon crystal that make up a protrusion 18 when viewed from a lesser or no magnification.

FIG. 8 illustrates a table of the wet chemical that caused the contamination illustrated in FIGS. 6A–6E. This wet chemical, an acid, should have percentage levels of the elements listed that are less than the number illustrated in the DL column. Of note, this acid, after being subjected to the test using the present invention as described above, was sent to an independent laboratory as is conventionally done. This test indicated that an undesirably large amount of copper was present. As a result, this test confirmed the present invention's ability to detect a metal contaminant in a wet chemical using the enhanced deposition growth process described previously.

Figure 7A:
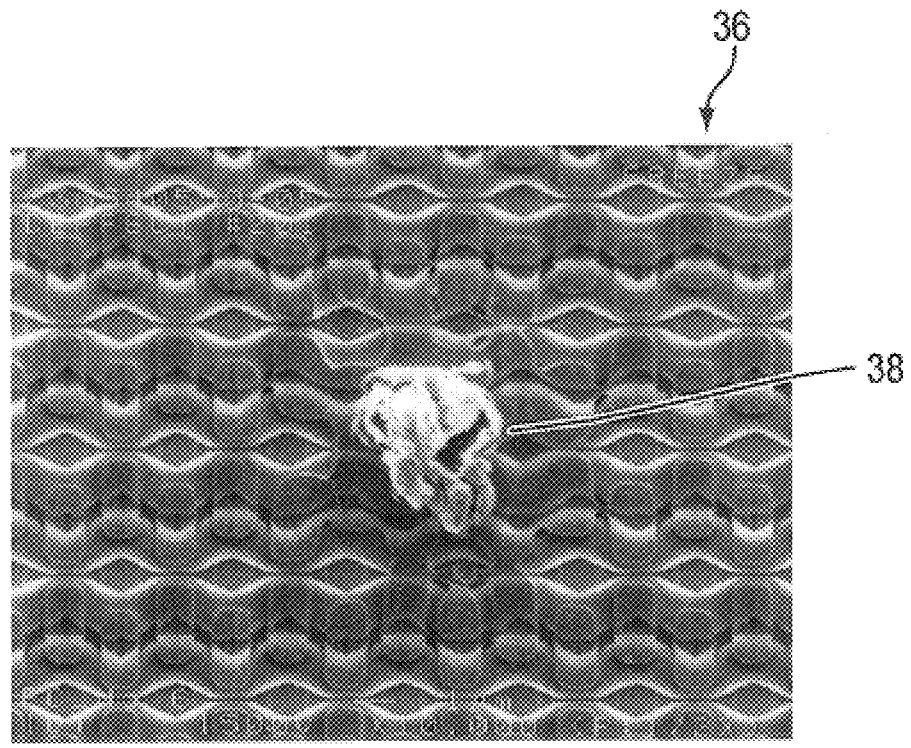
FIGS. 7A and 7B illustrate, at various magnifications, particle contamination that is distinct from the metal contamination being detected according to the preferred embodiment of the present invention.
Figure 7B:
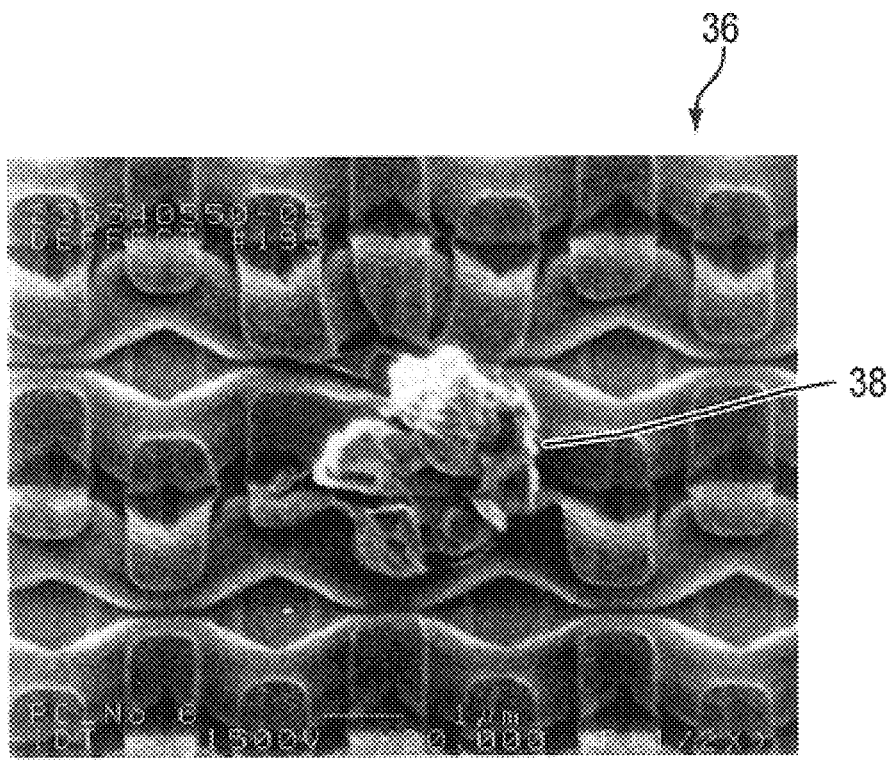

To assist in further illustrating how the undesired protrusions 18 differ from particle contamination, FIGS. 7A and 7B illustrate particle contamination 38 on a semiconductor wafer 36 at 15,000× and 30,000× magnification. At these magnifications, it is readily apparent how the protrusions 18, each containing many whiskers 34, differ from the illustrated particle contaminant 38. Also, it should be noted that the protrusions 18 that result due to there being metal contamination will be much more numerous on the surface on a single wafer than the number of particle contaminants that would be typically introduced. Accordingly, differentiation between particle contaminants and metal contaminants will exist after the semiconductor wafer has been processed as described according to the present invention.

Thus, as has been described by the foregoing, the presence of an undesired metal contaminant can be easily made in a relatively short period of time. As a result, the present invention can thus be used as a supplemental test for monitoring the quality of a wet chemical on a monthly, daily or even more frequent basis. Furthermore, the present invention can be used to access the desirability of introducing a new batch of chemicals into a process or implementing a new process that contains a new batch of chemicals. Still furthermore, the invention can be used to determine whether contamination has been introduced as a result of a wet chemical bath that contains worn out or wet bench parts. Accordingly, the present invention can assist in significantly reducing the down time of a semiconductor fabrication line.

While the preferred embodiment and details of the invention have been described above, it will be apparent to those skilled in the art that various changes and modification may be made without departing from the scope of the invention, as is defined by the claims below.

I claim:

1. A method of detecting metal contaminants that may exist in a wet chemical comprising the steps of:

wetting a semiconductor surface with said wet chemical;

drying said wet chemical on said semiconductor surface;

depositing a semiconductor material on said semiconductor surface at a temperature that is greater than about 400 degrees Celsius and a pressure that is less than about 5 Torr so that said metal contaminants that exist on said semiconductor surface will act as seeds and cause enhanced crystal growth of said semiconductor material on said semiconductor surface at locations corresponding to positions of said metal contaminants on said semiconductor surface; and inspecting said semiconductor surface after said step of depositing, the existence of said enhanced crystal growth indicating the presence of said metal contaminant in said wet chemical.

2. A method according to claim 1 wherein said step of depositing uses chemical vapor deposition.

3. A method according to claim 1 wherein said semiconductor material is polysilicon.

4. A method according to claim 2 wherein said temperature is greater than 600 degrees Celsius, said pressure is less than 1 Torr and a duration of said chemical vapor deposition is less than 10 minutes.

5. A method according to claim 4 wherein said semiconductor material is polysilicon.

6. A method according to claim 4 wherein said step of depositing lasts for a duration of less than 2 minutes.

7. A method according to claim 6 wherein said semiconductor material is polysilicon.

8. A method according to claim 7 wherein said step of inspecting uses a visual inspection of said semiconductor surface without magnification.

9. A method according to claim 7 wherein said step of inspecting uses a visual inspection of said semiconductor surface with magnification.

10. A method according to claim 1 wherein said step of inspecting uses a visual inspection of said semiconductor surface without magnification.

11. A method according to claim 1 wherein said step of inspecting uses a visual inspection of said semiconductor surface with magnification.

12. A method of introducing a new wet chemical into a semiconductor chip fabrication process comprising the steps of:

selecting said new wet chemical;

verifying that metal contaminants do not exist in said new wet chemical, said step of verifying comprising the steps of:

wetting a semiconductor surface with said new wet chemical;

drying said new wet chemical on said semiconductor surface;

depositing a semiconductor material on said semiconductor surface at a temperature that is greater than about 400 degrees Celsius and a pressure that is less than about 5 Torr so that said metal contaminants that exist on said semiconductor surface will act as seeds and cause enhanced crystal growth of said semiconductor material on said semiconductor surface at locations corresponding to positions of said metal contaminants on said semiconductor surface; and inspecting said semiconductor surface after said step of depositing, the existence of said enhanced crystal growth indicating the presence of said metal contaminant in said wet chemical; and using said new wet chemical in said semiconductor chip fabrication process once it has been verified that metal contaminants do not exist in said new wet chemical.

13. A method according to claim 12 wherein said step of depositing uses chemical vapor deposition.

14. A method according to claim 12 wherein said semiconductor material is polysilicon.

15. A method according to claim 13 wherein said temperature is greater than 600 degrees Celsius, said pressure is less than 1 Torr and a duration of said chemical vapor deposition is less than 10 minutes.

16. A method according to claim 15 wherein said semiconductor material is polysilicon.

17. A method according to claim 15 wherein said step of depositing lasts for a duration of less than 2 minutes.

18. A method according to claim 17 wherein said semiconductor material is polysilicon.

19. A method according to claim 18 wherein said step of inspecting uses a visual inspection of said semiconductor surface without magnification.

20. A method according to claim 18 wherein said step of inspecting uses a visual inspection of said semiconductor surface with magnification.

21. A method according to claim 12 wherein said step of inspecting uses a visual inspection of said semiconductor surface without magnification.

22. A method according to claim 12 wherein said step of inspecting uses a visual inspection of said semiconductor surface with magnification.

* * * * *